United States Patent
Wang et al.

(10) Patent No.: US 6,961,123 B1
(45) Date of Patent: Nov. 1, 2005

(54) METHOD AND APPARATUS FOR OBTAINING INFORMATION FROM POLARIZATION-SENSITIVE OPTICAL COHERENCE TOMOGRAPHY

(75) Inventors: Lihong Wang, College Station, TX (US); Shuliang Jiao, College Station, TX (US)

(73) Assignee: The Texas A&M University System, College Station, TX (US)

( * ) Notice: Subject to any disclaimer, the term of this patent is extended or adjusted under 35 U.S.C. 154(b) by 124 days.

(21) Appl. No.: 10/260,236

(22) Filed: Sep. 27, 2002

Related U.S. Application Data

(60) Provisional application No. 60/325,990, filed on Sep. 28, 2001.

(51) Int. Cl.[7] .................................................. G01J 4/00
(52) U.S. Cl. ...................................................... 356/364
(58) Field of Search ................................ 356/364–369; 250/225, 227.17

(56) References Cited

U.S. PATENT DOCUMENTS

| 6,043,887 A | * | 3/2000 | Allard et al. ................ 356/364 |
| 6,208,415 B1 | * | 3/2001 | De Boer et al. ............. 356/450 |
| 6,504,604 B1 | * | 1/2003 | Holland ....................... 356/73.1 |
| 6,538,738 B1 | * | 3/2003 | Okamoto ..................... 356/364 |
| 2002/0113972 A1 | * | 8/2002 | Rosenfeldt et al. ......... 356/477 |
| 2004/0036886 A1 | * | 2/2004 | Motamedi et al. .......... 356/477 |

OTHER PUBLICATIONS

Jose J. Gil and Eusebio Bernabeu, "*Obtainment of the polarizing and retardation parameters of a non–depolarizing optical system from the polar decomposition of its Mueller matrix*," Optik 76, No. 2, pp. 67–71, 1987.

N. Vansteenkiste, P. Vignolo, and A. Aspect, "*Optical reversibility theoems for polarization: application to remote control of polarization*," © 1993 Optical Society of America, J. Opt. Soc. Am. A, vol. 10, No. 10, pp. 2240–2245, Oct. 1993.

F. Le Roy–Brehonnet and B. Le Jeune, "*Utilization of Mueller Matrix Formalism to Obtain Optical Targets Depolarization and Polarization Properties*," © 1997 Elsevier Science Ltd., Prog. Quant. Electr. vol. 21, No. 2, pp. 109–151, 1997.

Johannes F. de Boer, Thomas E. Milner, Martin J.C. van Gemert, and J. Stuart Nelson, "*Two–dimensional birefringence imaging in biological tissue by polarization–sensitive optical coherence tomography*," © 1997 Optical Society of America, Optics Letters, vol. 22, No. 12, pp. 934–936, Jun. 15, 1997.

M. J. Everett, K. Schoenenberger, B. W. Colston, Jr., and L. B. Da Silva, *Birefringence characterization of biological tissue by use of optical coherence tomography*, © 1998 Optical Society of America, Optics Letters, vol. 23, No. 3, pp. 228–230, Feb. 1, 1998.

Johannes F. de Boer, Shyam M. Srinivas, Arash Malekafzali, Zhongping Chen, and J. Stuart Nelson, "*Imaging thermally damaged tissue by polarization sensitive optical coherence tomography*," © 1998 OSA, Optics Express, vol. 3, No. 6, pp. 212–218, Sep. 14, 1998.

(Continued)

Primary Examiner—Michael P. Stafira
(74) Attorney, Agent, or Firm—Baker Botts L.L.P.

(57) ABSTRACT

An apparatus includes a first section operable to detect polarization-sensitive radiation emitted by an object, and a second section operable to determine a Jones matrix based on information obtained by the first section from the polarization-sensitive radiation. The second section thereafter transforms the Jones matrix into a Mueller matrix, the Mueller matrix being representative of properties of the object.

27 Claims, 7 Drawing Sheets

OTHER PUBLICATIONS

Johannes F. de Boer, Thomas E. Milner, and J. Stuart Nelson, "Determination of the depth–resolved Stokes parameters of light backscattered from turbid media by use of polarization–sensitive optical coherence tomography," © 1999 Optical Society of America, Optics Letters, vol. 24, No. 5, pp. 300–302, Mar. 1, 1999.

Gang Yao and Lihong V. Wang, "Two–dimensional depth–resolved Mueller matrix characterization of biological tissue by optical coherence tomography," © 1999 Optical Society of America, Optics Letters, vol. 24, No. 8, pp. 537–539, Apr. 15, 1999.

Yonghua Zhao, Zhongping Chen, Christopher Saxer, Shaohua Xiang, Johannes F. de Boer, and J. Stuart Nelson, "Phase–resolved optical coherence tomography and optical Doppler tomography for imaging blood flow in human skin with fast scanning speed and high velocity sensitivity," © 2000 Optical Society of America, Optics Letters, vol. 25, No. 2, pp. 114–116, Jan. 15, 2000.

Shuliang Jiao, Gang Yao, and Lihong V. Wang, "Depth–resolved two–dimensional Stokes vectors of backscattered light and Mueller matrices of biological tissue measured with optical coherence tomography," © 2000 Optical Society of America, Applied Optics, vol. 39, No. 34, pp. 6318–6324, Dec. 1, 2000.

* cited by examiner

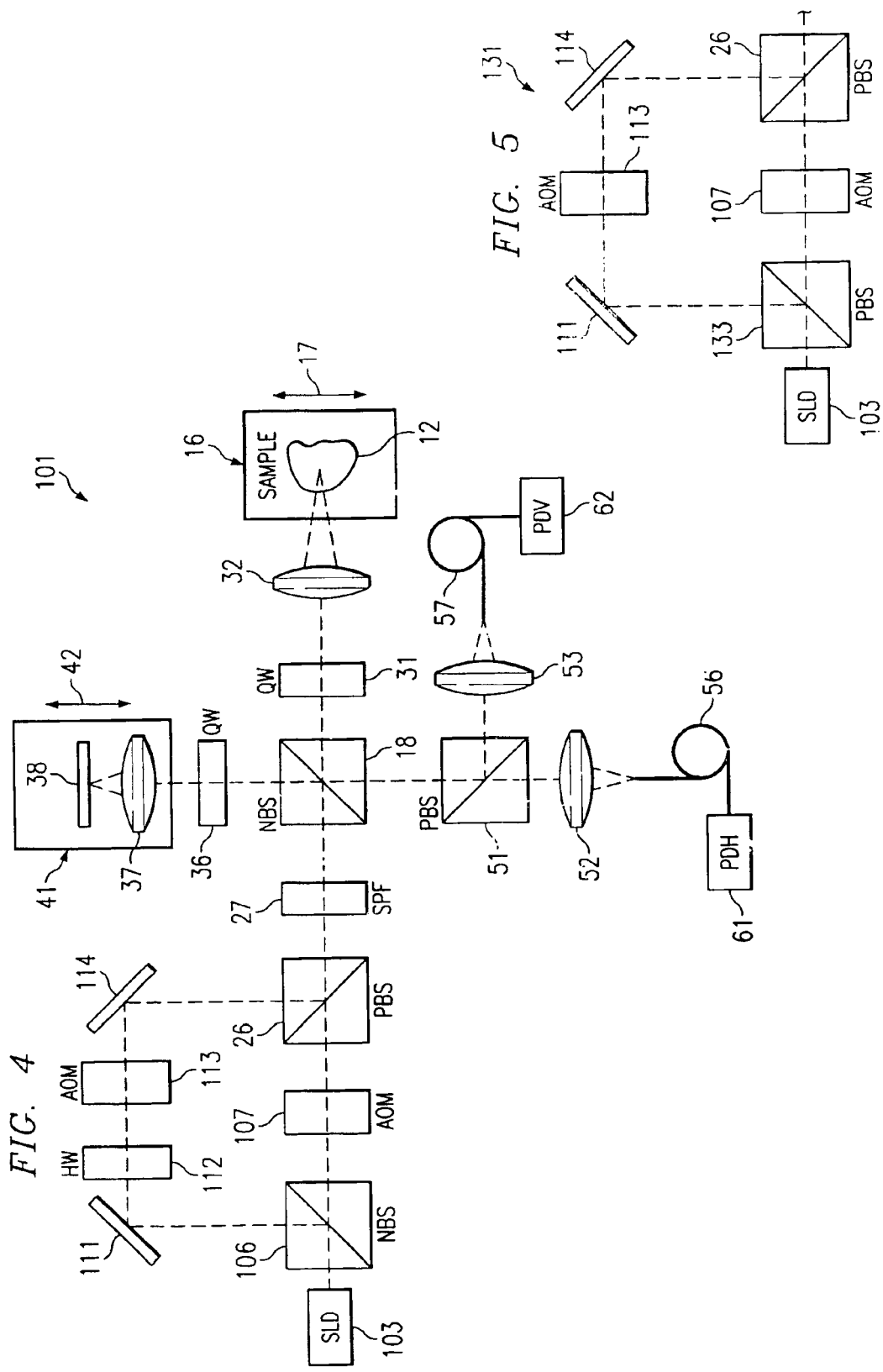

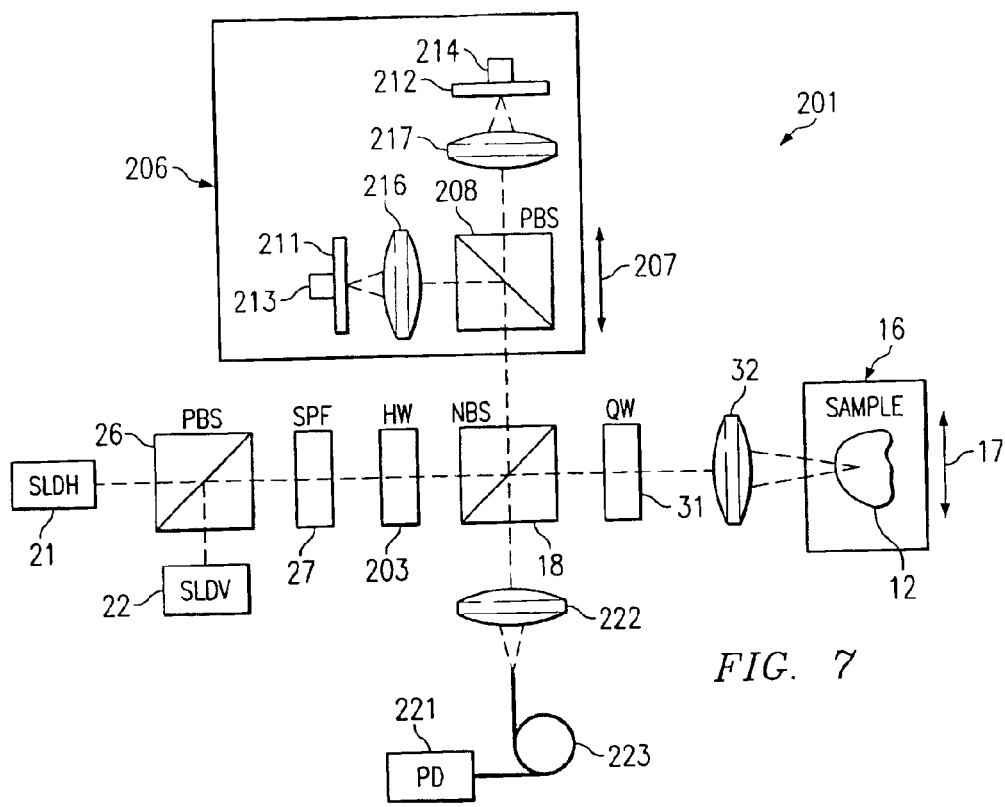
FIG. 7
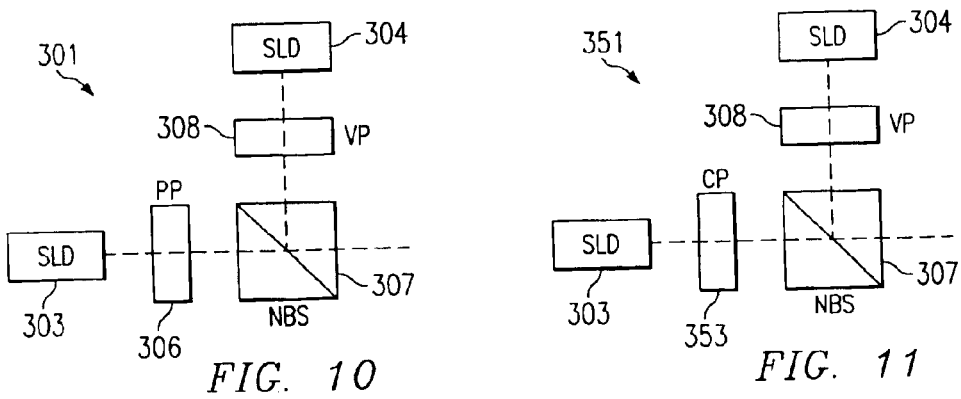
FIG. 10
FIG. 11

METHOD AND APPARATUS FOR OBTAINING INFORMATION FROM POLARIZATION-SENSITIVE OPTICAL COHERENCE TOMOGRAPHY

This application claims the priority under 35 U.S.C. §119 of provisional application No. 60/325,990 filed Sep. 28, 2001.

GOVERNMENT RIGHTS

This invention was made with government support under Contract Nos. R21 RR15368 and R01 CA71980 awarded by the National Institutes of Health, and by National Science Foundation grant BES-9734491. The government has certain rights in this invention.

TECHNICAL FIELD OF THE INVENTION

The present invention relates generally to techniques for analyzing radiation and, more particularly, to techniques for obtaining information from polarization-sensitive radiation.

BACKGROUND OF THE INVENTION

It is known that one good way to ascertain the optical polarization properties of an object or sample is to determine its Mueller matrix. By using polarimetry in combination with optical coherence tomography (OCT), the Mueller matrix of a sample can be acquired with OCT resolution. The degree of polarization (DOP) of the back-scattered light measured with OCT remains unity throughout the detection range, indicating that the measured Mueller matrix is non-depolarizing.

However, existing techniques for measuring the Mueller matrix of a sample are relatively time consuming. As a practical matter, the relatively time-consuming nature of these existing techniques effectively limits their use to stable samples, such as bones. These existing techniques are generally not suitable for measuring the Mueller matrix of an unstable sample, such as soft tissue. For an unstable sample such as biological tissue, it would typically be necessary to determine the Mueller matrix during a single scan of the type known in the art as an A scan, and existing systems are not sufficiently fast to do this.

SUMMARY OF THE INVENTION

One form of the present invention involves: causing an object to emit polarization-sensitive radiation; detecting the polarization-sensitive radiation; determining a Jones matrix based on information obtained in the detecting step from the polarization-sensitive radiation; and transforming the Jones matrix into a Mueller matrix, the Mueller matrix being representative of properties of the object.

BRIEF DESCRIPTION OF THE DRAWINGS

A better understanding of the present invention will be realized from the detailed description which follows, taken in combination with the accompanying drawings, in which:

FIG. 4 is a block diagram of an apparatus which is an alternative embodiment of the apparatus of FIG. 1;

FIG. 5 is a block diagram of an apparatus which is an alternative embodiment of a portion of the apparatus of FIG. 4;

FIG. 7 is a block diagram of an apparatus which is still another alternative embodiment of the apparatus of FIG. 1;

FIG. 10 is a block diagram of an apparatus which is an alternative embodiment of part of the apparatus of FIG. 1; and FIG. 11 is a block diagram of an apparatus which is an alternative embodiment of the apparatus of FIG. 10.

DETAILED DESCRIPTION

Figure 1:
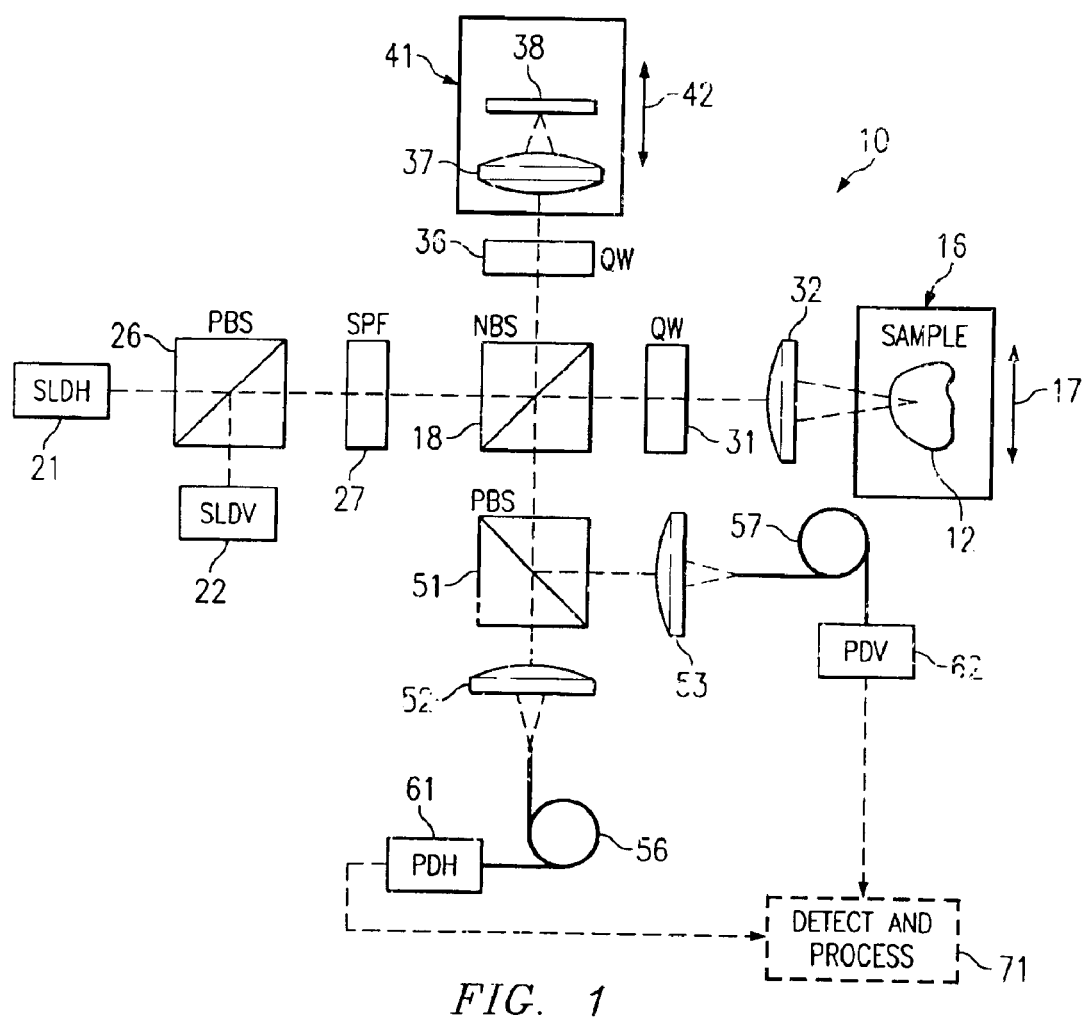
FIG. 1 is a block diagram of a polarization-sensitive optical coherence tomography (OCT) apparatus, which embodies aspects of the present invention.

FIG. 1 is a block diagram of a polarization-sensitive optical coherence tomography (OCT) apparatus 10, which embodies aspects of the present invention. As discussed in more detail later, the apparatus 10 uses polarization-sensitive OCT to optically and non-destructively collect information about a sample 12. The sample 12 is not itself a part of the apparatus 10, and may be biological tissue, such as cartilage, collagen, or a retina. Alternatively, the sample 12 could be a non-biological material, such as a piece of a polymer material. Through the use of polarization properties as a contrast mechanism, polarization-sensitive OCT can reveal some information about biological tissue or other material that is not available with conventional OCT techniques.

The apparatus 10 includes a translation stage in the form of a table 16, which has the sample 12 supported thereon, and which is supported for reciprocal linear movement in directions indicated by a double-headed arrow 17. Movement of the table 16 permits a linear lateral scan of the sample 12. The apparatus 10 further includes a non-polarizing beam splitter 18, which is disposed functionally at the center of the apparatus 10. The portion of the apparatus to the left of the splitter 18 is referred to as the source arm, the portion above the splitter 18 is referred to as the reference arm, the portion to the right of the splitter 18 is referred to as the sample arm, and the portion below the splitter 18 is referred to as the detection arm.

The source arm to the left of the splitter 18 includes two superluminescent diodes 21 and 22, which each serve as a low-coherence light source having a central wavelength of approximately 850 nm, and a full width at half maximum (FWHM) bandwidth of 26 nm. The diodes 21 and 22 are respectively modulated at 3 KHz and 3.5 KHz. The two source beams from the diodes 21 and 22 travel to and are merged by a polarizing beam splitter 26. The composite optical signal travels to and is filtered by a spatial filter assembly 27, and then travels to a non-polarizing beam splitter 18.

The beam from the diode 21 is split into two components by the splitter 18, one of which travels upwardly into the reference arm, and the other of which travels rightwardly into the sample arm. Similarly, the beam from the diode 22 is split into two components by the splitter 18, and these two components respectively travel upwardly into the reference arm and rightwardly into the sample arm.

The sample arm to the right of the splitter 18 includes a quarter wave plate, the fast axis of which is oriented at 45°. The sample arm also includes an objective lens 32, with f=15 mm and NA=0.15. Radiation from the splitter 18 passes through the plate 31 and is focused by the lens 32 onto the sample 12. A portion of this radiation is reflected, and travels back through the lens 32 and plate 31 to the splitter 18.

The reference arm above the splitter 18 includes a quarter wave plate 36, a lens 37, and a mirror 38. The lens 37 and mirror 38 are supported on a table 41, which in turn is supported for reciprocal linear movement in directions indicated by a double-headed arrow 42. A not-illustrated mechanism moves the table 41 reciprocally for depth scan, and generates a carrier frequency of approximately 1.2 KHz.

As mentioned above, the splitter 18 directs two beam components into the reference arm, and these beam components travel upward through the plate 36, and are focused by the lens 37 onto the mirror 38. Substantially all of this radiation is reflected by the mirror 38, and travels back through the lens 37 and plate 36 to the splitter 18. The fast axis of the plate 36 is oriented at 22.5°. Consequently, after these components pass through the plate 36 twice, the component representing horizontal polarization is converted into 45° polarization, while the component representing vertical polarization is converted into −45° polarization.

The components reflected by the sample 12 and the components reflected by the mirror 38 arrive back at the splitter 18, and are combined by the splitter 18. This combined light beam travels downwardly from the splitter 18 into the detector arm, where it is split into two orthogonal polarization components by a polarizing beam splitter 51. These two components each pass through a respective objective lens 52 or 53, and are each coupled into a respective single-mode optical fiber 56 or 57. At the opposite end of each of the fibers 56 and 57 is a respective photodiode 61 or 62. The photodiode 61 detects the horizontal component of the radiation, and the photodiode 62 detects the vertical component of the radiation. The outputs of the photodiodes 61 and 62 are each coupled to a circuit 71 which has a portion that serves as a data acquisition system, the circuit 71 detecting and processing the information produced by the diodes 61 and 62. In the disclosed embodiment, the circuit 71 digitizes the output of each diode in a known manner at a sampling rate of about 50,000 samples per second.

Turning now to the issue of how the data collected by the circuit 71 is analyzed, it is known in the art that one good way to ascertain the optical polarization properties of an object or sample is to determine its Mueller matrix. By using polarimetry in combination with OCT, the Mueller matrix of a sample can be acquired with OCT resolution. However, existing techniques for measuring the Mueller matrix of a sample are relatively time consuming. As a practical matter, the relatively time-consuming nature of these existing techniques effectively limits their use to stable samples, such as bones. These existing techniques are generally not suitable for measuring the Mueller matrix of an unstable sample, such as soft tissue. In particular, for an unstable sample such as biological tissue, it would be necessary to determine the Mueller matrix during a single scan of the type known in the art as an A scan, and existing systems were not sufficiently fast to do this.

According to one feature of the present invention, a different approach is taken. In particular, the depth-resolved 2×2 Jones matrix J of a sample is acquired during a single A scan, in a manner discussed in more detail later. The 2×2 Jones matrix J is then transformed into an equivalent 4×4 Mueller matrix.

In more detail, a Mueller matrix is suitable for all kinds of optical systems, but a Jones matrix can only be applied to a non-depolarizing optical system. In a non-depolarizing optical system, a Jones matrix can completely characterize the polarization properties of the optical system. In other words, for a non-depolarizing optical system, a Jones matrix is equivalent to a Mueller matrix. An aspect of the present invention relates to experimental proof that the degree of polarization (DOP) of back-scattered light measured with OCT remains unity throughout the detection range, indicating that the measured Mueller matrix is non-depolarizing. This in turn means that an equivalent Jones matrix can be used instead of the Mueller matrix.

A Jones matrix is a 2×2 matrix based on complex numbers, whereas a Mueller matrix is a 4×4 matrix based on real numbers. A Jones matrix has four complex elements, in which one phase is arbitrary. Consequently, seven real parameters are independent. Equivalently, there are seven independent parameters in a non-depolarizing Mueller matrix.

A Jones matrix (J) transforms an input Jones vector ($E_{IN}$) into an output Jones vector ($E_{OUT}$), while a Mueller matrix (M) transforms an input Stokes vector ($S_{IN}$) into an output Stokes vector ($S_{OUT}$):

$$E_{OUT} = \begin{bmatrix} E_{OH} \\ E_{OV} \end{bmatrix} = JE_{IN} = \begin{bmatrix} J_{11} & J_{12} \\ J_{21} & J_{22} \end{bmatrix} \begin{bmatrix} E_{iH} \\ E_{iV} \end{bmatrix}, \quad (1)$$

$$S_{OUT} = \begin{bmatrix} S_0 \\ S_1 \\ S_2 \\ S_3 \end{bmatrix} = MS_{IN} = \begin{bmatrix} M_{00} & M_{01} & M_{02} & M_{03} \\ M_{10} & M_{11} & M_{12} & M_{13} \\ M_{20} & M_{21} & M_{22} & M_{23} \\ M_{30} & M_{31} & M_{32} & M_{33} \end{bmatrix} \begin{bmatrix} S_{i0} \\ S_{i1} \\ S_{i2} \\ S_{i3} \end{bmatrix}, \quad (2)$$

where $E_{OH}$ and $E_{OV}$ are the horizontal and vertical components of the electric vector of the output light field; $E_{iH}$ and $E_{iV}$ are the horizontal and vertical components of the electric vector of the input light field; $S_0$, $S_1$, $S_2$ and $S_3$ are the elements of the Stokes vector of the output light; and $S_{i0}$, $S_{i1}$, $S_{i2}$ and $S_{i3}$ are the elements of the Stokes vector of the input light, respectively.

The Jones matrices of a homogenous partial polarizer ($J_P$) and a homogenous elliptical retarder ($J_R$) can be expressed as $$J_P = \begin{bmatrix} P_1\cos^2\alpha + P_2\sin^2\alpha & (P_1 - P_2)\sin\alpha\cos\alpha e^{-i\Delta} \\ (P_1 - P_2)\sin\alpha\cos\alpha e^{i\Delta} & P_1\sin^2\alpha + P_2\cos^2\alpha \end{bmatrix}, \quad (3)$$

$$J_R = \begin{bmatrix} e^{i\varphi/2}\cos^2\theta + e^{-i\varphi/2}\sin^2\theta & (e^{i\varphi/2} - e^{-i\varphi/2})\sin\theta\cos\theta e^{-i\delta} \\ (e^{i\varphi/2} - e^{-i\varphi/2})\sin\theta\cos\theta e^{-i\delta} & e^{i\varphi/2}\sin^2\theta + e^{-i\varphi/2}\cos^2\theta \end{bmatrix},$$

where $P_1$, $P_2$ are the principal coefficients of the amplitude transmission for the two orthogonal polarization eigenstates; $\alpha$ is the orientation of $J_P$; $\varphi$ and $\theta$ are the retardation and orientation of $J_R$; and $\Delta$ and $\delta$ are the phase differences for the vertical and horizontal components of the eigenstates of $J_P$ and $J_R$, respectively. A retarder is called elliptical when its eigenvectors are those of elliptical polarization states. A polarizing element is called homogeneous when the two eigenvectors of its Jones matrix are orthogonal. The Jones-matrix of a non-depolarizing optical system can be transformed into an equivalent non-depolarizing Mueller matrix by the following relationship:

$$M = U(J \otimes J^*)U^{-1} \quad (4A)$$

$$= U \begin{bmatrix} J_{11}J^* & J_{12}J^* \\ J_{21}J^* & J_{22}J^* \end{bmatrix} U^{-1}$$

$$= U \begin{bmatrix} J_{11}J_{11}^* & J_{11}J_{12}^* & J_{12}J_{11}^* & J_{12}J_{12}^* \\ J_{11}J_{21}^* & J_{11}J_{22}^* & J_{12}J_{21}^* & J_{12}J_{22}^* \\ J_{21}J_{11}^* & J_{21}J_{12}^* & J_{22}J_{11}^* & J_{22}J_{12}^* \\ J_{21}J_{21}^* & J_{21}J_{22}^* & J_{22}J_{21}^* & J_{22}J_{22}^* \end{bmatrix} U^{-1};$$

and a Jones vector of a light field can be transformed into a Stokes vector by $$S = \sqrt{2}\, U(E \otimes E^*) = \sqrt{2}\, U \begin{bmatrix} E_H E^* \\ E_V E^* \end{bmatrix} \quad (4B)$$

$$= \sqrt{2}\, U \begin{bmatrix} E_H E_H^* \\ E_H E_V^* \\ E_V E_H^* \\ E_V E_V^* \end{bmatrix},$$

where $\otimes$ represents the Kronecker tensor product and U is the 4×4 Jones-Mueller transformation matrix:

$$U = \frac{1}{\sqrt{2}} \begin{bmatrix} 1 & 0 & 0 & 1 \\ 1 & 0 & 0 & -1 \\ 0 & 1 & 1 & 0 \\ 0 & i & -i & 0 \end{bmatrix}.$$

At least two independent incident polarization states, which are not necessarily orthogonal, are needed to fully determine a Jones matrix.

As mentioned above, the portions of the apparatus 10 of FIG. 1 which are above and to the right of the splitter 18 are respectively referred to as the reference arm and the sample arm. For OCT signals based on single-backscattered photons, the incident Jones vector $E_i$ to the sample arm is transformed to the detected Jones vector $E_o$ by $$E_o = J_{NBS}J_{QB}J_{SB}J_M J_{SI}J_{QI}E_i \quad (5)$$

$$= J_{NBS}J_{QB}JJ_{QI}E_i = J_T E_i$$

where $J_{QI}$ and $J_{QB}$ are the Jones matrices of a quarter wave plate for the incident and backscattered light, respectively; $J_{SI}$ and $J_{SB}$ are the Jones matrices of the sample for the incident and backscattered light, respectively; $J_M$ is the Jones matrix of the single backscatterer (the same Jones matrix as for a mirror); $J_{NBS}$ is the Jones matrix of the reflecting surface of the non-polarizing beam splitter; J is the combined round-trip Jones matrix of the scattering medium; and $J_T$ is the overall round-trip Jones matrix.

In Equation (5), the output Jones vector $E_O$ is constructed for each light source from the measured horizontal and vertical components of the OCT signal. Upon acquiring the output Jones vectors, and knowing the input Jones vectors, the overall round-trip Jones matrix $J_T$ can be calculated. The Jones matrix J of the sample can be extracted from $J_T$ by eliminating the effect of the Jones matrices of the quarter wave plate, the mirror and the beam splitter. As a necessary condition, the two light sources must be independent of each other, which means that there is an arbitrary phase difference between the two measured Jones vectors for the two light sources. The arbitrary phase difference must be eliminated in order to calculate $J_T$.

In the commonly used convention, $J_M$ transforms the polarization state of the forward light expressed in the forward coordinate system into the polarization state expressed in the backward coordinate system. Similarly, $J_{NBS}$ transforms the polarization state of the backward light into the polarization state expressed in the detection coordinate system. However, the polarization states of both the forward and backward light are expressed here in the forward coordinate system. In this convention, $J_M$ and $J_{NBS}$ are unitary:

$$J_M = J_{NBS} = \begin{bmatrix} 1 & 0 \\ 0 & 1 \end{bmatrix}.$$

In each A-scan, the optical paths for the forward and backward light are the same, and therefore the Jones' reversibility theorem can be applied. The Jones reversibility theorem indicates that the Jones matrices $J_{BWD}$ and $J_{FWD}$ of an ordinary optical element for the backward and forward light propagations have the following relationship if the same coordinate system is used for the Jones vectors: $J_{BWD} = J_{FWD}^T$. Therefore, the following relationships apply:

$$J_{SB} = J_{SI}^T, \quad J_{QB} = J_{QI}^T = \frac{1}{\sqrt{2}} \begin{bmatrix} 1 & i \\ i & 1 \end{bmatrix},$$

$$J = J_{SB}J_M J_{SI} = J_{SI}^T J_{SI} = J^T,$$

$$J_T = J_{NBS}J_{QB}JJ_{QI} = J_{QI}^T JJ_{QI} = J_T^T.$$

In other words, matrices J and $J_T$ are transpose symmetric. This property of transpose symmetry is significant in regard to eliminating the arbitrary phase difference between the two light sources. Because of this symmetry, the number of independent parameters in the Jones matrix is further reduced from seven to five.

For the multiply scattered photons, Equation (5) still holds if the probabilities for photons to travel along the same round-trip path but in opposite directions are equal, which is a valid assumption when the source and detector have reciprocal characteristics. Because these photons are coherent, the round-trip Jones matrix of the sample J is the sum of the Jones matrices of all the possible round-trip paths; and for each possible path—for example, the k-th path—the round-trip Jones matrix is the sum of the Jones matrices for the two opposite directions [$J_i(k)$ and $J_r(k)$]. Consequently, it follows that:

$$J = \sum_k [J_i(k) + J_r(k)] = \sum_k \{J_i(k) + [J_i(k)]^T\} = J^T.$$

In other words, J as well as $J_T$ still possesses the transpose symmetry even if multiple scattering occurs, so long as the source and the detector meet the condition.

After calculation, Equation (5) can be expressed as $$\begin{bmatrix} E_{oH} \\ E_{oV} \end{bmatrix} = \begin{bmatrix} \frac{i}{2}(J_{11} - 2iJ_{12} - J_{22}) & \frac{1}{2}(J_{11} + J_{22}) \\ \frac{1}{2}(J_{11} + J_{22}) & \frac{i}{2}(-J_{11} - 2iJ_{12} + J_{22}) \end{bmatrix} \times \begin{bmatrix} E_{iH} \\ E_{iV} \end{bmatrix} \quad (6A)$$

$$= \begin{bmatrix} J_{T11} & J_{T12} \\ J_{T12} & J_{T22} \end{bmatrix} \times \begin{bmatrix} E_{iH} \\ E_{iV} \end{bmatrix},$$

where $J_{ij}$ and $J_{Tij}$ (i,j=1,2) are the elements of J and $J_T$, respectively. For two light sources of independent polarization states, Equation (6A) can be rearranged as $$\begin{bmatrix} E_{oH1} & E_{oH2} \\ E_{oV1} & E_{oV2} \end{bmatrix} = \begin{bmatrix} J_{T11} & J_{T12} \\ J_{T12} & J_{T22} \end{bmatrix} \times \begin{bmatrix} E_{iH1} & E_{iH2}e^{i\beta} \\ E_{iV1} & E_{iV2}e^{i\beta} \end{bmatrix}, \quad (6B)$$

where $E_{oH1}$ and $E_{oH2}$, $E_{oV1}$ and $E_{oV2}$ are the elements of the Jones vectors of source 1 and source 2, respectively; and β is the random initial phase-difference between the two light sources due to the mutual independence of them. $J_T$ can be calculated from Equation (6B) as $$\begin{bmatrix} J_{T11} & J_{T12} \\ J_{T12} & J_{T22} \end{bmatrix} = \begin{bmatrix} E_{oH1} & E_{oH2} \\ E_{oV1} & E_{oV2} \end{bmatrix} \times \begin{bmatrix} E_{iH1} & E_{iH2}e^{i\beta} \\ E_{iV1} & E_{iV2}e^{i\beta} \end{bmatrix}^{-1} \quad (6C)$$

$$= \frac{1}{D} \begin{bmatrix} E_{oH1} & E_{oH2} \\ E_{oV1} & E_{oV2} \end{bmatrix} \times \begin{bmatrix} E_{iV2}e^{i\beta} & -E_{iH2}e^{i\beta} \\ -E_{iV1} & E_{iH1} \end{bmatrix},$$

so long as the determinant $$D = \begin{vmatrix} E_{iH1} & E_{iH2}e^{i\beta} \\ E_{iV1} & E_{iV2}e^{i\beta} \end{vmatrix} = e^{i\beta} \begin{vmatrix} E_{iH1} & E_{iH2} \\ E_{iV1} & E_{iV2} \end{vmatrix} \neq 0,$$

or in other words, the two light sources are not in the same polarization state. The random phase difference β can be eliminated with the transpose symmetry of $J_T$.

$$e^{\beta}(E_{oH1}E_{iH2}+E_{oV1}EiV2)=(E_{ov2}E_{iV1}+E_{oH2}E_{ih1}). \quad (6D)$$

Equation (6D) can solved when $(E_{oH1}E_{iH2}+E_{oV1}E_{iV2}) \neq 0$. Once $J_T$ is found, J can then be determined from $J_T$. Six real parameters of J can be calculated, in which one phase is arbitrary and can be subtracted from each element, and eventually five independent parameters are retained.

When $(E_{oH1}E_{iH2}+E_{oV1}E_{iV2})=0$, it is not possible to eliminate the random phase by using the transpose symmetry. This situation happens if, aside from producing a mirror reflection, the sample arm does not alter the polarization states of the two incident beams. For example, this situation occurs if (1) a horizontal or vertical incident beam is used, (2) a quarter wave plate is not inserted in the sample arm, and (3) the fast axis of a birefringent sample is horizontal or vertical. The use of the quarter wave plate at a 45° orientation in the sample arm can ameliorate the situation. However, there are still some drawbacks with this configuration. For example, when the round-trip Jones matrix J is equivalent to that of a half wave plate with its fast axis oriented at 45°, and thus $J_T$ is equivalent to a unitary matrix, then $(E_{oH1}E_{iH2}+E_{oV1}E_{iV2})=0$. To overcome this drawback, it is possible to employ two non-orthogonal incident polarization states, for example where one source is in a horizontal polarization state and the other source is in a 45° polarization state.

In the circuit 71, the interference signals measured by the photodiodes 61 and 62 are bandpass filtered with central frequencies of 4.2 KHz and 4.7 KHz and a bandwidth of 10 Hz, in order to extract the interference components of each light source. In this regard, 4.2 KHz and 4.7 KHz are the harmonic frequencies of the interference signals H and V of the horizontal source 21 and the vertical source 22, respectively. The interference components form the imaginary parts of the analytical signals $E_{x,y}(t)$, whose real parts are obtained through inverse Hilbert transformation:

$$Re\{E_{x,y}(t)\} = \frac{1}{\pi} P \int_{-\infty}^{\infty} \frac{Im\{E_{x,y}(\tau)\}}{\tau-t} d\tau, \quad (7)$$

where P stands for the Cauchy principal value of the integral, and x and y represent the detected polarization state (H or V) and the source polarization state (H or V), respectively.

Unlike other transforms, the Hilbert transformation does not change the domain. A convenient method of computing the Hilbert transform is by means of the Fourier transformation. If u(t) and v(t) are a Hilbert pair of functions, that is $$u(t) \stackrel{H}{\Longleftrightarrow} v(t)$$

and U(w) and V(w) are the Fourier transforms of u(t) and v(t), the following can be used to calculate the Hilbert transform:

$$u(t) \stackrel{F}{\Rightarrow} U(w) \Rightarrow V(w) = -i \cdot sgn(w)U(w) \stackrel{F^{-1}}{\Longrightarrow} v(t) \quad (8)$$

$$v(t) \stackrel{F}{\Rightarrow} V(w) \Rightarrow U(w) = i \cdot sgn(w)U(w) \stackrel{F^{-1}}{\Longrightarrow} u(t),$$

where F and $F^{-1}$ denote the Fourier and inverse Fourier transformations, respectively; and sgn(w) is the signum function defined as $$sgn(w) = \begin{cases} +1 & w > 0 \\ 0 & w = 0 \\ -1 & w < 0 \end{cases}.$$

The real and imaginary parts of each interference component are combined to form the complex components of the output Jones vectors. Upon determining the output Jones vector, when the input Jones vectors are known, the elements of the Jones matrix J of the sample can then be calculated from Equation (6).

Figure 2:
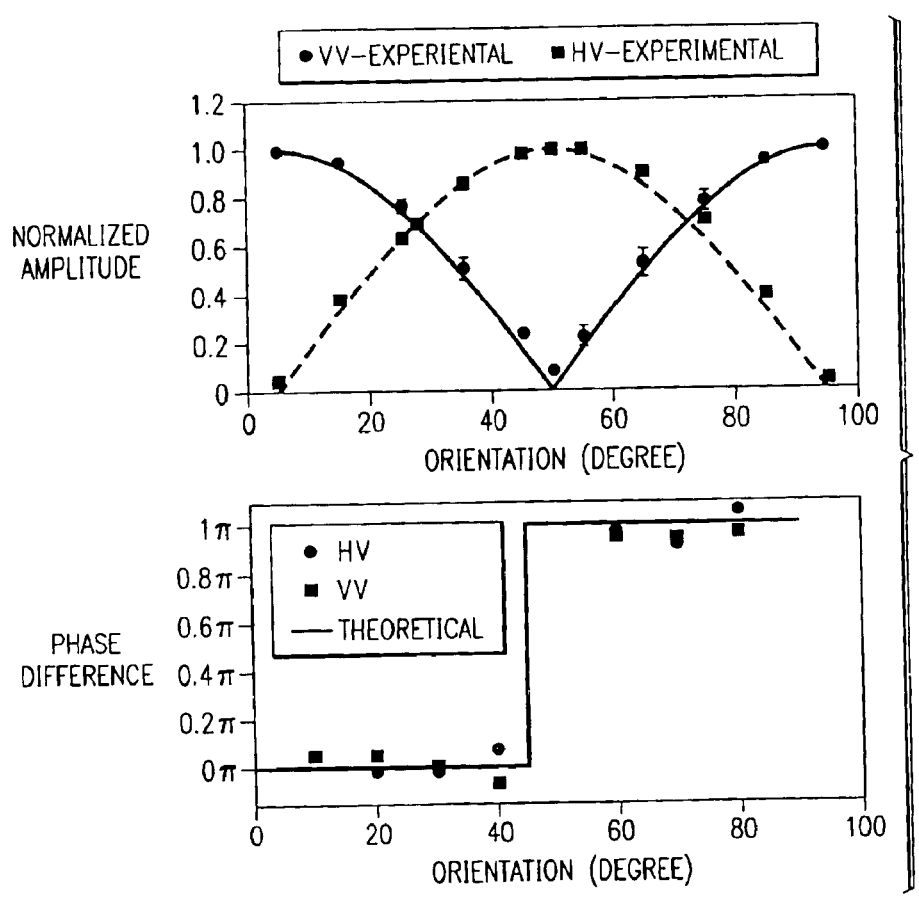
FIG. 2 includes two related graphs which are respectively presented in the upper and lower portions thereof.

The apparatus 10 of FIG. 1 was subjected to some initial testing, which involved measuring the matrix of a quarter wave plate at various orientations in combination with a mirror. The upper and lower portions of FIG. 2 are two related graphs. The graph in the upper portion of FIG. 2 shows the amplitude of the vertical components of the measured Jones vector versus the orientation of the quarter wave plate, where the amplitude of each Jones vector was normalized to unity. The graph in the lower portion of FIG. 2 shows the phase differences between the vertical components and the horizontal components of the Jones vectors. The results were calculated by averaging more than 1000 points centered at the peak of the interference signals, where adjacent points have a spacing which corresponds to a 10-μm resolution of the system. The graphs in FIG. 2 show that the measured data agrees very well with the theoretical data.

After verifying the operational characteristics of the apparatus 10 with these initial tests, the apparatus 10 was used to image an actual sample of soft tissue. In particular, a piece of porcine tendon was mounted in a cuvette filled with saline solution. The sample was transversely scanned with a step size of 5 μm through movement of the table 16 in a direction parallel to the arrow 17, and multiple A-scan images were taken.

Figure 3:
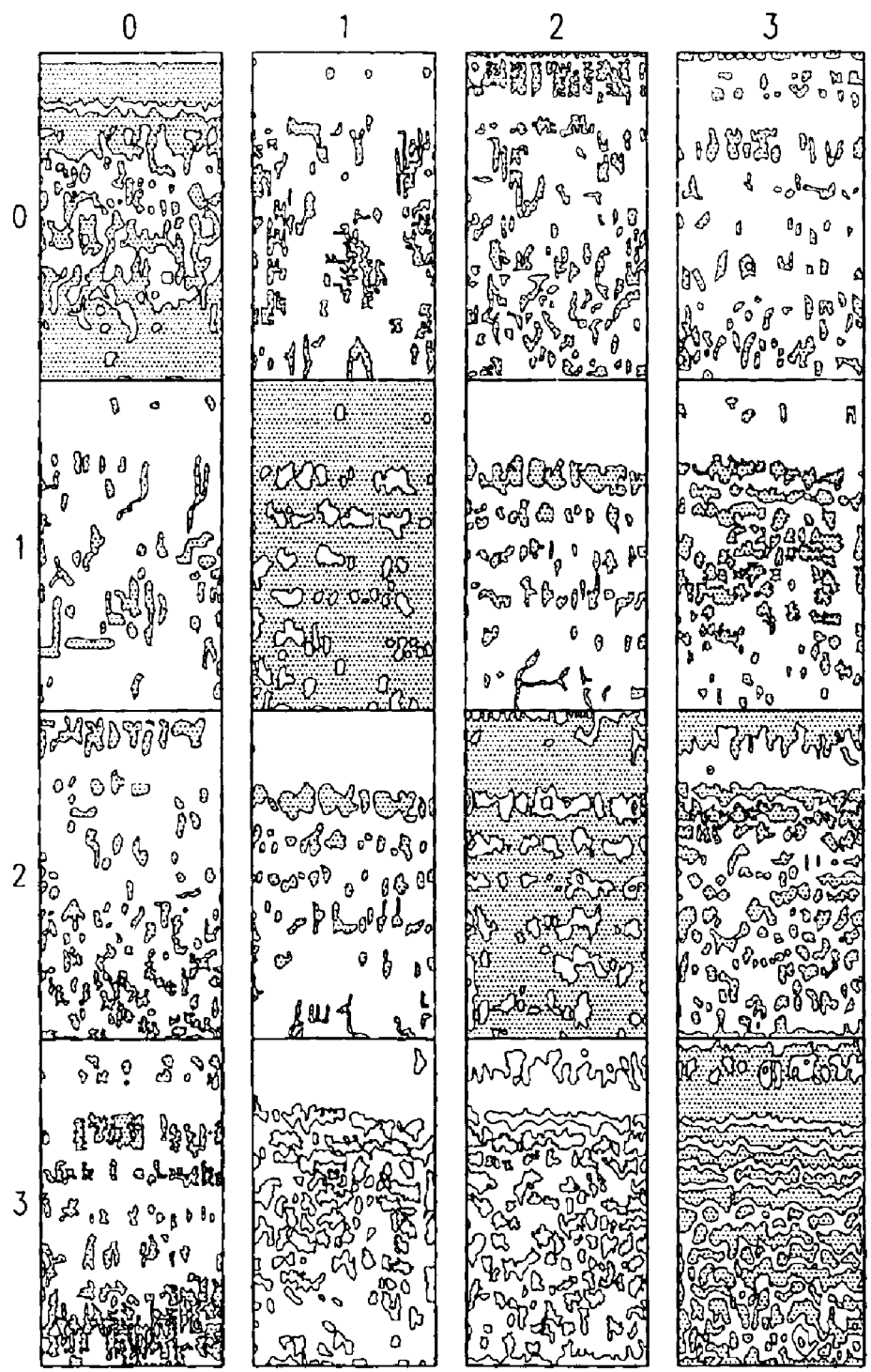
FIG. 3 is a diagrammatic view of an array of Mueller matrix images obtained using techniques according to the present invention.

The interference signals were first band-pass filtered and Hilbert transformed in the manner discussed above, in order to extract the analytical signals of each polarization component. The analytical signals were then demodulated. For each A scan, pixels were formed by averaging the calculated elements of the Jones matrix over segments of 1000 points. Two-dimensional (2D) images were formed from these A-scan images, and were then median filtered. Then, each 2D Mueller-matrix image was pixel-wise normalized with an $M_{00}$ image. The resulting 2D images are shown in FIG. 3. In this discussion, each reference which is in the form $M_{XY}$ represents a reference to the image appearing in row X and column Y of FIG. 3. In FIG. 3, each image corresponds to a size of 0.5 mm by 1.0 mm.

Clear band structures can be seen in some of the images, especially in $M_{13}$, $M_{22}$, $M_{23}$, $M_{31}$, $M_{32}$, and $M_{33}$. There is no such band structure present in the $M_{00}$ image, which is the image based on the intensity of the back-scattered light. In other words, the $M_{00}$ image is free of the effect of polarization. It is believed that the band structure is generated by the birefringence of the collagen fibers in the porcine tendon. The band structure distributes quite uniformly in the measured region. Therefore, the birefringence is also uniform in the measured area.

The foregoing discussion has been directed to a technique for efficiently acquiring a Mueller matrix of a sample. However, acquisition of the Mueller matrix of a sample is only a first step. Once the Mueller matrix has been obtained, it can be decomposed in order to extract significant information regarding the optical polarization properties of the sample, such as retardation, orientation of the major axes, and diattenuation. The polarization properties may be correlated to the normal or abnormal condition of biological tissue.

A non-depolarizing Mueller matrix can be decomposed by polar decomposition:

$$M = M_P M_R, \text{ or } M = M'_R M'_P, \quad (9)$$

where $M_P$ and $M'_P$ are the Mueller matrices of a diattenuator (partial polarizer), and $M_R$ and $M'_R$ are the Mueller matrices of an elliptical retarder. To verify the decomposition, polarization information was extracted from a piece of porcine tendon at various orientations. If only linear diattenuation is considered, elements $M_{31}$ and $M_{32}$ in Equation (4) become:

$$M_{31} = P_1 P_2 \sin(2\theta) \sin(\delta), \text{ and } M_{32} = -P_1 P_2 \cos(2\theta) \sin(\delta), \quad (10)$$

where $P_1$, $P_2$ are the principal coefficients of the amplitude transmission for the two orthogonal polarization eigenstates of the partial polarizer; $\theta$ is the orientation of the fast axis of the retarder; and $\delta$ is the phase retardation of the retarder. The calculated 2D images of $M_{31}$ and $M_{32}$ were averaged over segments of twenty A scans, and were fitted for a physical depth of 0.4 mm from the surface, assuming that the sample has a refractive index of n=1.4. The calculated retardation from the fitted data is $(4.2\pm0.3)\times10^{-3}$, which is comparable to a known value of $(3.7\pm0.4)\times10^{-3}$ for bovine tendon. The calculated angles of the fast axis for tissue fiber orientations varying with an interval of 10° are $(0\pm4)°$, $(9\pm2.9)°$, $(20.9\pm1.9)°$, $(30\pm2.8)°$ and $(38\pm4.3)°$ after subtracting an offset angle. The small angular offset is due to the discrepancy between the actual and the observed fiber orientations. The results were very good, considering that the tendon was slightly deformed when it was mounted in the cuvette, and the center of rotation for the sample may not have been exactly collinear with the optical axis. The diattenuation, defined as $$D = (P_1^2 - P_2^2)/(P_1^2 + P_2^2) = \sqrt{M_{01}^2 + M_{02}^2 + M_{03}^2} \Big/ M_{00},$$

was averaged over all of the orientations, and linearly fitted over a depth of 0.3 mm. The fitted diattenuation D versus the round-trip physical path length increased with a slope of 0.26/mm, and reached 0.075±0.024 at a depth of 0.3 mm, after subtracting an offset at the surface.

Alternative Embodiments

FIG. 4 is a block diagram of an apparatus 101 which is an alternative embodiment of the apparatus 10 of FIG. 1. The apparatus 101 of FIG. 4 differs from the apparatus 10 of FIG. 1 primarily in regard to the configuration of the source arm, or in other words the portion of the apparatus to the left of the non-polarizing beam splitter 18. Parts in FIG. 4 which are equivalent to parts in FIG. 1 are identified with the same reference numerals.

The apparatus 101 includes a superluminescent diode 103, which is equivalent to either of the diodes 21 or 22 of FIG. 1. The radiation emitted by the diode 103 is polarized, and travels to a non-polarizing beam splitter 106. The splitter 106 splits the beam from the diode 103 into two separate beams of equal intensity, one of which then passes through an acousto-optical modulator (AOM) 107 of a known type, and the other of which is reflected by a mirror 111 and then passes through a half wave plate 112 and a modulator 113. The plate 112 is oriented at 45°, and converts the beam into its orthogonal polarization state. The modulators 107 and 113 modulate the two beams at different frequencies, which are respectively 3 KHz and 3.5 KHz.

The modulated beam from the modulator 107 travels to the polarizing beam splitter 26, and the modulated beam from the modulator 113 is reflected by a mirror 114 and then travels to the splitter 26. The splitter 26 merges the two modulated beams in the manner discussed above in associated with FIG. 1. The remaining portion of FIG. 4 is generally similar to the corresponding portion of FIG. 1, and is therefore not described here in detail.

As evident from FIG. 4, one of the two beams from the splitter 106 follows a longer path than the other beam in order to reach the splitter 26. The difference between the lengths of these two paths is much longer than the coherence length of the optical beam from the diode 103. Consequently, when the splitter 26 combines the component beams, the resulting combined light beam is equivalent to a light beam merged from two independent light sources of difference modulation frequencies with orthogonal polarization states.

FIG. 5 is a block diagram of an apparatus 131 which is an alternative embodiment of a portion of the source arm in the apparatus 101 of FIG. 4. Equivalent parts are identified by the same reference numerals, and only the differences are discussed in detail. In particular, the half wave plate 112 of FIG. 4 is omitted in the apparatus of FIG. 5, and the non-polarizing beam splitter 106 of FIG. 4 is replaced with a polarizing beam splitter 133. The beam from the diode 103 is polarized at 45°, and is split by the splitter 133 into two beams having orthogonal polarization states. The remainder of the apparatus 131 is similar in structure and operation to the corresponding portion of the apparatus 101 of FIG. 4.

Figure 6:
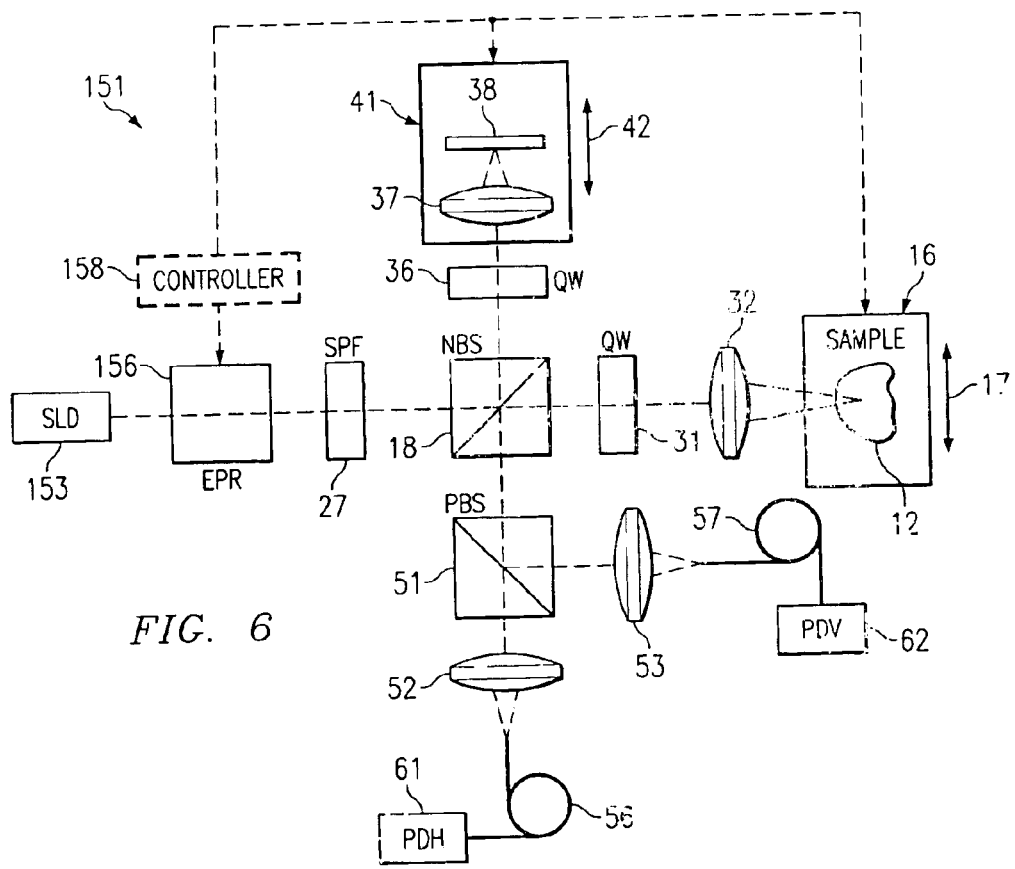
FIG. 6 is a block diagram of an apparatus which is yet another alternative embodiment of the apparatus of FIG. 1.

FIG. 6 is a block diagram of an apparatus 151 which is yet another alternative embodiment of the apparatus 10 of FIG. 1. Parts in FIG. 6 which are equivalent to parts in FIG. 1 are identified with the same reference numerals, and only significant differences are described here. The primary differences are in the configuration of the source arm, which as discussed above is the portion of the apparatus to the left of the splitter 18.

The apparatus 151 includes a superluminescent diode 153, which emits radiation that travels to an electrically controlled polarization rotator (EPR) 156. The EPR 156 is a commercially available device of a known type. The EPR 156 is controlled by a controller 158, which also controls the movement of tables 16 and 41. The controller 158 causes the EPR 156 to alternately switch in a cyclic manner between two different operational modes. In one operational mode, the radiation from diode 153 which is passing through the EPR 156 is given a first polarization state, and in the other mode the radiation from diode 153 is given a second polarization state orthogonal to the first polarization state. In other words, this is a time division or time sharing approach, in which the photodiodes 61 and 62 are alternately operated to detect information for respective polarization states in successive alternating time slots, rather than being operated simultaneously as in the embodiment of FIG. 1.

FIG. 7 is a block diagram of an apparatus 201 which is still another alternative embodiment of the apparatus 10 of FIG. 1. Equivalent parts are identified with the same reference numerals, and only the differences are described below. The source arm to the left of the splitter 18 is similar to the source arm in FIG. 1, except that a half wave plate 203 is provided between the filter 27 and the splitter 18. As discussed earlier, the diodes 21 and 22 are modulated at different frequencies. When the two source beams from these diodes reach the half wave plate 203, they are converted into +45° (P) and −45° (M) polarization states.

In the reference arm, a table 206 is supported for linear reciprocal movement in directions indicated by a double-headed arrow 207. A polarizing beam splitter 208 is supported on the table 206. The table 206 also supports a piezoelectric transducer (PZT) 213 and a piezoelectric transducer 214, each of which movably supports a respective mirror 211 or 212. A lens 216 is disposed between the splitter 208 and mirror 211, and a lens 217 is disposed between the splitter 208 and mirror 212. The transducers 213 and 214 are driven with signals having different frequencies, so that the transducers effect vibration of the mirrors 211 and 212 at different frequencies.

The two beam components which travel into the reference arm from the splitter 18 are each split by the splitter 208 into two subcomponents, which each pass through a respective lens 216 or 217, and are each reflected by a respective mirror 211 or 212. The reflected subcomponents then pass back through the respective lenses 216 and 217, and are combined by the splitter 208. The resulting beam is returned to the splitter 18. Since the mirrors 211 and 212 are vibrated at different frequencies, they introduce different modulation frequencies into the horizontal and vertical polarization states represented by the respective subcomponents. As a result, the detection arm of the apparatus 201 needs only a single photodiode 221 to effect detection for the two orthogonal polarization components, rather than two separate photodiodes such as those shown at 61 and 62 in FIG. 1. The reference arm includes an objective lens 222, which directs radiation received from the splitter 18 into one end of a single-mode optical fiber 223. The opposite end of the fiber 223 is connected to the photodiode 221.

Figure 8:
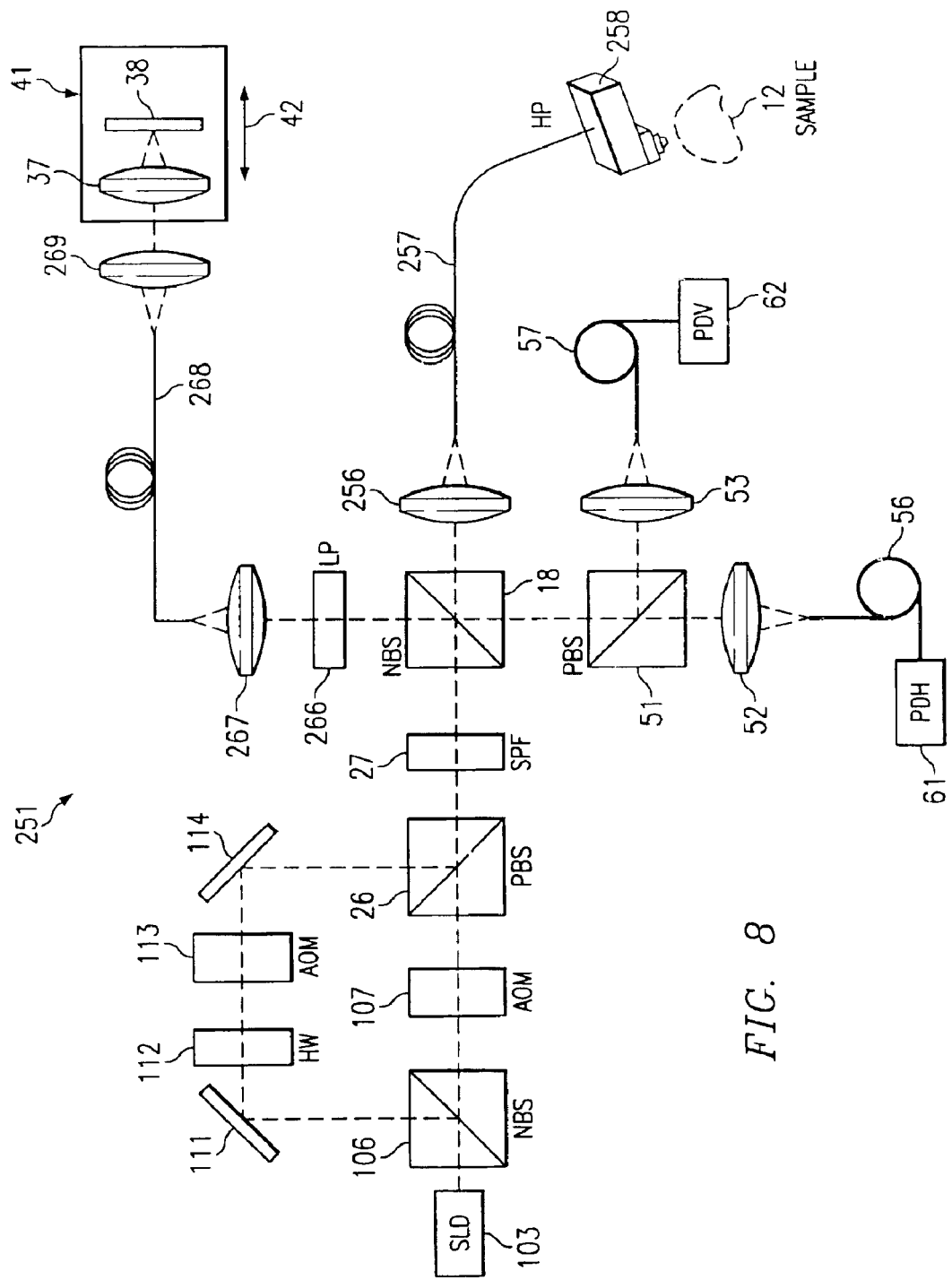
FIG. 8 is a block diagram of an apparatus which is another alternative embodiment of the apparatus of FIG. 4.

FIG. 8 is a block diagram of an apparatus 251 which is an alternative embodiment of the apparatus 101 shown in FIG. 4. Equivalent parts are identified with the same reference numerals, and only significant differences are described in detail below. In the sample arm, radiation from the splitter 18 passes through an objective lens 256, which directs the radiation into one end of a single-mode optical fiber 257. A hand-held probe (HP) 258 is provided at the other end of the fiber 257, and serves as an imaging head.

Figure 9:
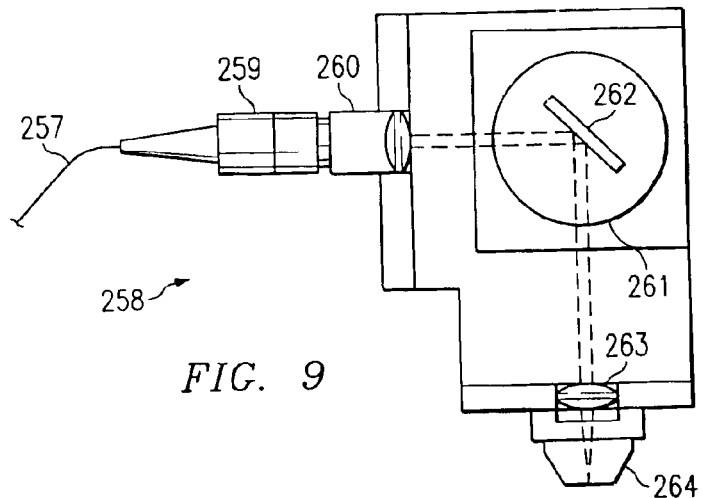
FIG. 9 is a diagrammatic sectional side view of a hand-held probe which is a component of the apparatus of FIG. 8.

FIG. 9 is a diagrammatic sectional side view of the hand-held probe 258. The end of the fiber 257 is coupled by a connector 259 to a fiber collimator, through which a beam of radiation enters the probe 258. The probe has a motor 261 powered by a not-illustrated source, which can effect limited reciprocal pivotal movement of a mirror 262. A lens 263 and a window 264 are supported on a housing of the probe 258. The beam from the collimator 260 is reflected by the mirror 262, and passes through the lens 263 and the window 264 to the sample 12 (FIG. 8). Radiation reflected from the sample 12 travels back through the window 264 and lens 263, is reflected again by the mirror 262, and then travels back through the collimator 260 and into the fiber 257. The movement of the mirror 262 by the motor 261 causes the beam impinging on the sample 12 to be linearly scanned across the sample.

Radiation which travels into the reference arm from the splitter 18 passes through a linear polarizer (LP) 266 oriented at 45°. This radiation then passes through a lens 267, which directs it into a single-mode optical fiber 268. When the radiation emerges from the opposite end of the fiber 268, it passes through a lens 269, and then through the lens 37 on the movable table 41. This radiation is then reflected by the mirror 38, and travels back through the lens 37, lens 269, fiber 268, lens 267 and linear polarizer 266 to the splitter 18.

FIG. 10 is a block diagram of an alternative embodiment of part of the apparatus of FIG. 1 and, in particular, is an alternative embodiment of part of the source arm of FIG. 1. The apparatus 301 would be utilized in a situation where the sample 12 (FIG. 1) does not happen to alter the polarization state of the light impinging on it, such that an orthogonal incident polarization arrangement of the type discussed above would not provide accurate phase information for the backscattered light. The apparatus 301 therefore uses polarization states for the two incident beams which are non-orthogonal, in that one is vertically polarized and the other is polarized at ±45°.

More specifically, the apparatus 301 includes two superluminescent diodes 303 and 304. The beam from the diode 303 is polarized at 45° by a polarization plate (PP) 306, and the beam from the diode 304 is vertically polarized by a vertical polarization (VP) plate 308. The beams from the plates 306 and 308 are each supplied to a non-polarizing beam splitter 307, which combines these beams. The resulting beam is then supplied to a spatial filter of the type shown at 27 in FIG. 1.

FIG. 11 is a block diagram of an apparatus 351 which is an alternative embodiment of the apparatus 301 of FIG. 10. Equivalent parts are identified by the same referenced numerals. The primary difference is that the polarizing plate 306 of FIG. 10 is replaced with a circular polarization plate 353, which is a one-eighth wave plate oriented at 22.5°. The plates 353 and 308 respectively give the two beams circular and vertical polarizations.

Advantages

The present invention provides a number of technical advantages. One such advantage is that, when using polarization-sensitive OCT imaging, Mueller matrix images of an object can be obtained with a single scan. On a more specific level, the Jones matrix of the sample is determined during the single scan, and then the Jones matrix is transformed into an equivalent Mueller matrix. This facilitates the acquisition of two-dimensional tomographic Mueller-matrix images of an unstable sample such as biological tissue, either in vivo or in vitro. A further advantage is that the image information has relatively high spatial resolution. Yet another advantage is that the Mueller matrix can be decomposed in order to extract information on optical polarization properties of the sample, such as retardation, orientation of the major axes, and diattenuation. The polarization properties may be correlated to normal or abnormal conditions of biological tissues.

Although several selected embodiments have been illustrated and described in detail, it should be understood that various substitutions and alterations are possible without departing from the spirit and scope of the present invention, as defined by the following claims.

What is claimed is:

1. A method, comprising the steps of:
    causing an object to emit polarized radiation by:
        transmitting predetermined radiation to said object;
        generating first and second optical beams having different polarizations; and
        splitting each of said first and second beams into first and second components, said first components each being directed to said object to cause said object to emit said polarized radiation;
    directing each of said second components to a reference section where each said second component is reflected by a reflective surface which is physically modulated to thereby generate modulated components;
    forming further radiation from said modulated components and said polarized radiation;
    detecting said polarized radiation comprising said further radiation;
    determining a Jones matrix based on information obtained in said detecting step from said polarized radiation; and
    transforming said Jones matrix into a Mueller matrix, said Mueller matrix being representative of properties of said object.

2. A method according to claim 1, including the step of decomposing said Mueller matrix to obtain information representative of optical polarization properties of said object.

3. A method according to claim 1, including the step of selecting an unstable material as said object.

4. A method according to claim 3, wherein said step of selecting said unstable material includes the step of selecting biological tissue as said object.

5. A method according to claim 1, wherein said step of causing said object to emit polarized radiation involves polarization-sensitive optical coherence tomography.

6. A method according to claim 1,
    wherein said transmitting step includes the step of scanning said predetermined radiation physically across said object; and
    wherein said Jones matrix is determined from information obtained in said detecting step during a single said scan.

7. A method according to claim 1, including the step of selecting optical radiation as said predetermined radiation, said polarized radiation being optical radiation.

8. A method according to claim 7, wherein said predetermined radiation includes first and second portions which have different polarizations.

9. A method according to claim 1, wherein said step of generating said first and second optical beams is carried out by generating said first and second optical beams successively in time.

10. A method according to claim 1, wherein said step of generating said first and second optical beams is carried out by simultaneously generating said first and second optical beams.

11. A method according to claim 1, including the steps of:
    providing first and second detectors; and
    splitting said further radiation into two components which are each routed to a respective one of said detectors.

12. A method according to claim 11, including the step of configuring said reference section so that each said second component is reflected by the same reflective surface.

13. A method according to claim 1, including the steps of:
    configuring said reference section to have two of said reflective surfaces which are physically modulated at different frequencies, each of said second components being reflected by a respective one of said reflective surfaces; and
    routing said further radiation to one detector which effects said detecting step.

14. A method according to claim 1, including the steps of:
    providing a first optical fiber, said first components and said polarized radiation traveling through said first optical fiber in respective directions which are opposite; and
    configuring said reference section to include a second optical fiber, said second components and said modulated components traveling through said second optical fiber in respective directions which are opposite.

15. An apparatus, comprising:
    a first section operable to detect polarized radiation emitted by an object;
    a second section operable to determine a Jones matrix based on information obtained by said first section from said polarized radiation, and to thereafter transforms said Jones matrix into a Mueller matrix, said Mueller matrix being representative of properties of the object; and
    a third section operable to transmit to the object predetermined radiation which causes the object to emit said polarized radiation, said third section comprising:
        a source section which generates first and second optical beams having different polarizations;
        a splitter which splits each of said first and second beams into first and second components;
        a sample section which directs said first components to the object to cause the object to emit said polarized radiation and which directs said polarized radiation from the object to said splitter; and
        a reference section which is operable to cause each said second component to be reflected by a reflective surface which is physically modulated to thereby generate modulated components;
        wherein said splitter is operable to form further radiation from said modulated components and said polarized radiation, said first section being responsive to said further radiation.

16. An apparatus according to claim 15, wherein said second section is operable to decompose said Mueller matrix to obtain information representative of optical polarization properties of the object.

17. An apparatus according to claim 15,
    wherein said third section is operable to scan said predetermined radiation physically across the object; and
    wherein second section is operable to effect said determination of said Jones matrix from information obtained during a single said scan.

18. An apparatus according to claim 15, wherein said predetermined radiation is optical radiation, and said polarized radiation is optical radiation.

19. An apparatus according to claim 18, wherein said predetermined radiation includes first and second portions which have different polarizations.

20. An apparatus according to claim 15, wherein said source section generates said first and second optical beams successively in time.

21. An apparatus according to claim 15, wherein said source section generates said first and second optical beams simultaneously.

22. An apparatus according to claim 15, wherein said first section includes first and second detectors; and including a splitter which splits said further radiation into two components that are each routed to a respective one of said detectors.

23. An apparatus according to claim 22, wherein said reference section effects said reflection of each of said second components using the same reflective surface.

24. An apparatus according to claim 15, wherein said reference section includes two of said reflective surfaces which are physically modulated at different frequencies, each of said second components being reflected by a respective one of said reflective surfaces; and wherein said first section includes one detector which effects said detection of said polarized radiation.

25. An apparatus according to claim 15, wherein said sample section includes a first optical fiber, said first components and said polarized radiation traveling through said first optical fiber in respective directions which are opposite; and wherein said reference section includes a second optical fiber, said second components and said modulated components traveling through said second optical fiber in respective directions which are opposite.

26. An apparatus according to claim 25, including at an end of said first optical fiber remote from said splitter a hand-held probe which can be manually moved relative to the object.

27. An apparatus according to claim 26, wherein said hand-held probe includes structure operable to effect a scanning movement of a direction in which said first components are emitted from said probe.

* * * * *